(12) United States Patent
    Grüebler et al.

(10) Patent No.: US 12,589,028 B2
(45) Date of Patent: Mar. 31, 2026

(54) GRASPING STRUCTURE FOR MEMBRANE REMOVAL

(71) Applicant: Alcon Inc., Fribourg (CH)

(72) Inventors: Reto Grüebler, Greifensee (CH); Luca Palmerini, Basel (CH)

(73) Assignee: Alcon Inc., Fribourg (CH)

( * ) Notice: Subject to any disclaimer, the term of this patent is extended or adjusted under 35 U.S.C. 154(b) by 136 days.

(21) Appl. No.: 18/530,564

(22) Filed: Dec. 6, 2023

(65) Prior Publication Data

US 2024/0197525 A1 Jun. 20, 2024

Related U.S. Application Data

(60) Provisional application No. 63/387,331, filed on Dec. 14, 2022.

(51) Int. Cl.
    *A61F 9/007* (2006.01)
    *A61B 17/30* (2006.01)
(52) U.S. Cl.
    CPC .......... *A61F 9/00736* (2013.01); *A61B 17/30* (2013.01)
(58) Field of Classification Search
    CPC ................. A61F 9/00736; A61B 17/30; A61B 2017/305
    See application file for complete search history.

(56) References Cited

U.S. PATENT DOCUMENTS

| | | |
|---|---|---|
| 6,908,476 B2 | 6/2005 | Jud |
| 6,945,984 B2 | 9/2005 | Arumi |
| 9,320,534 B2 | 4/2016 | Vezzu |
| 9,827,141 B2 | 11/2017 | Schaller |
| 10,500,090 B2 | 12/2019 | Gunn et al. |
| 10,729,504 B2 | 8/2020 | Schaller |
| 10,973,682 B2 | 4/2021 | Vezzu et al. |
| 11,224,539 B2 | 1/2022 | Grueebler |
| 11,490,915 B2 | 11/2022 | Abt |
| 11,751,909 B2 | 9/2023 | Schaller |
| 11,759,237 B2 | 9/2023 | Schaller |
| 2005/0059988 A1 | 3/2005 | Danitz |
| 2014/0135820 A1 | 5/2014 | Schaller et al. |

(Continued)

FOREIGN PATENT DOCUMENTS

| | | | |
|---|---|---|---|
| AU | 2018292547 A1 | 12/2019 | |
| WO | WO-2005048854 A2 * | 6/2005 | ............ A61B 17/30 |
| WO | 2022079547 A1 | 4/2022 | |

OTHER PUBLICATIONS

U.S. Appl. No. 19/081,206, filed Mar. 17, 2025.
Alcon Surgical Retina Product Catalog, 2019 (36 pages).

*Primary Examiner* — Anh T Dang
(74) *Attorney, Agent, or Firm* — Patterson + Sheridan, LLP

(57) ABSTRACT

An ophthalmic surgical instrument for peeling a retinal membrane includes a handle and an actuator mounted on the handle. An outer tube is mounted to the handle and an inner rod extends within the outer tube. A grasping structure is secured to a distal end of the inner rod having first and second polymer arms secured to the inner rod. Each of the first polymer arm and the second polymer arms has a distal end that is angled to conform to the retinal membrane. The actuator is configured to control relative position of the inner rod and the outer tube in order to extend the grasping structure out of the outer tube and withdraw the grasping structure within the outer tube.

17 Claims, 7 Drawing Sheets

(56)  References Cited

U.S. PATENT DOCUMENTS

| 2015/0238355 | A1* | 8/2015 | Vezzu | A61F 9/00736 |
| | | | | 606/207 |
| 2016/0296246 | A1 | 10/2016 | Schaller | |
| 2019/0000670 | A1* | 1/2019 | Grueebler | A61F 9/00736 |
| 2022/0117779 | A1 | 4/2022 | Hallen | |
| 2024/0197526 | A1 | 6/2024 | Grüebler et al. | |
| 2024/0197527 | A1 | 6/2024 | Grüebler | |
| 2024/0197528 | A1 | 6/2024 | Grüebler et al. | |
| 2024/0197529 | A1 | 6/2024 | Grüebler et al. | |

* cited by examiner

GRASPING STRUCTURE FOR MEMBRANE REMOVAL

BACKGROUND

The internal limiting membrane (ILM) is a thin transparent membrane positioned between the vitreous and the retina of the eye. The ILM plays a role during the formation of the eye but is not required for the proper function of an adult eye. The ILM may pull at the retina and cause conditions such as macular holes, macular pucker, vitreo-macular traction syndrome, diabetic macular edema, and cystoid macular edema secondary to inflammation or venous occlusive diseases and other conditions. An epiretinal membrane (ERM) is a membrane that may form over the retina in response to damage to the retina, such as due to posterior vitreous detachment.

The ILM or ERM may need to be peeled away from the retina to prevent damage to the retina. Peeling of the ILM or ERM may also be required in preparation for surgical procedures performed on the retina. To peel the ILM or ERM, a surgical instrument is inserted through a cannula within the patient's eye globe. Forceps or a specialized scraper are extended from the instrument and used to raise a flap in the ILM or ERM. The flap is then grasped by the forceps and the ILM or ERM is peeled away from the retina using a circular motion. Excess force on the forceps may, however, result in piercing of the retina.

Accordingly, it would be an advancement in the art to reduce the risk of retinal damage resulting from membrane peeling.

BRIEF SUMMARY

The present disclosure relates generally to a membrane peeling tool including a grasping structure having flexible polymer arms with angled end surfaces.

An ophthalmic surgical instrument for peeling a retinal membrane includes a handle and an actuator mounted on the handle. An outer tube has a proximal end mounted to the handle and defining a longitudinal direction. An inner rod extends within the outer tube. A grasping structure is secured to a distal end of the inner rod. The grasping structure includes a first polymer arm and a second polymer arm secured to the inner rod and biased outwardly from one another along a transverse direction perpendicular to the longitudinal direction. Each of the first polymer arm and the second polymer arms has a distal end that is at an angle between 0 and 90 degrees (e.g., between 10 and 60 degrees) relative to a vertical direction that is perpendicular to the longitudinal direction and the transverse direction. The actuator is configured to control relative position of the inner rod and the outer tube in order to extend the grasping structure out of the outer tube and withdraw the grasping structure within the outer tube.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide a surgical instrument including a grasping structure with flexible polymer arms for peeling a membrane from a patient's retina. Note that, herein, a distal end of a component refers to the end that is closer to a patient's body while the proximal end of the component refers to the end that is facing away from the patient's body or in proximity to, for example, the handle of the surgical instrument.

Figure 1:
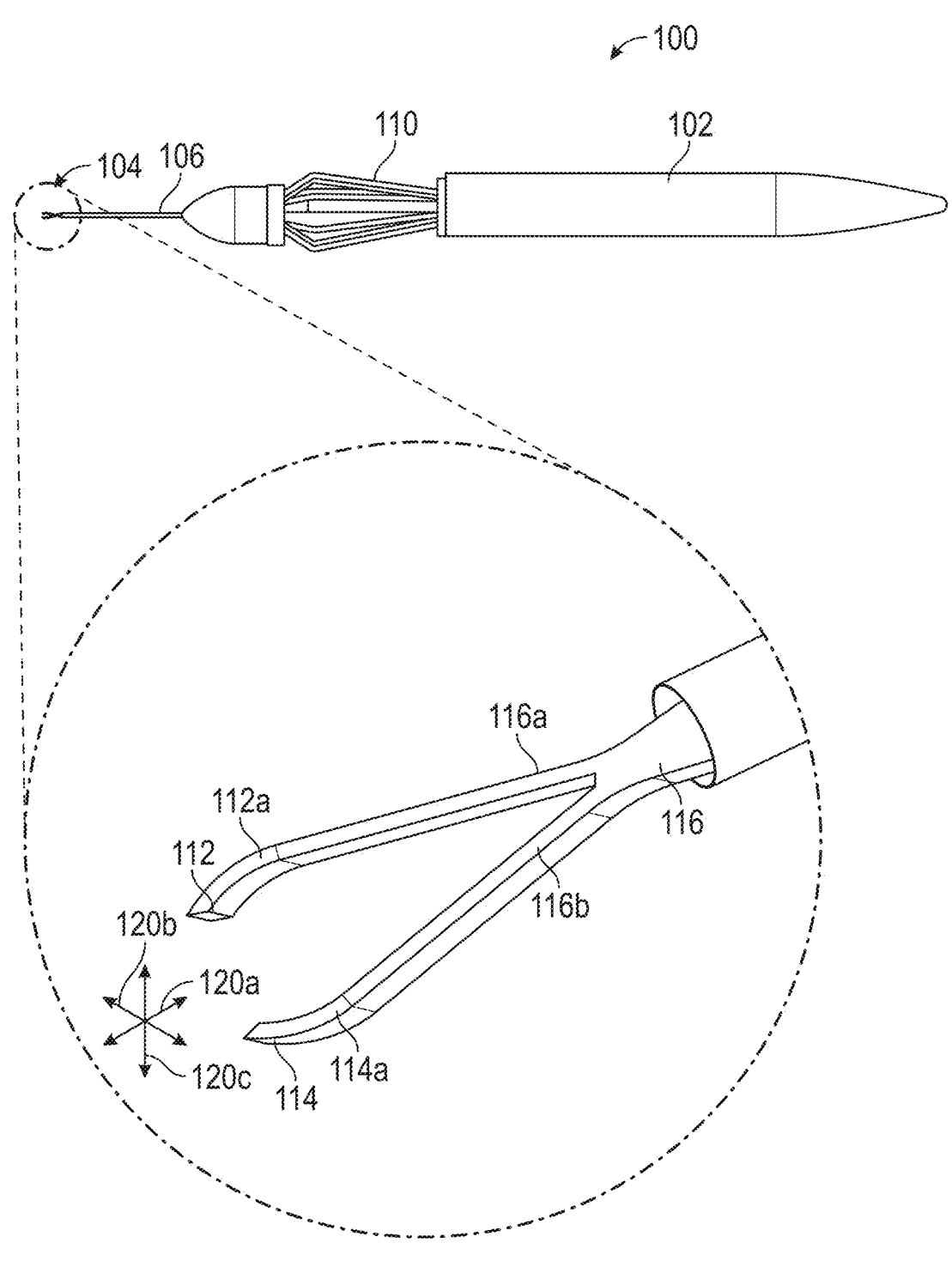
FIG. 1 is an isometric view of a surgical instrument having a grasping structure including flexible polymer arms, in accordance with certain embodiments.

FIG. 1 illustrates a surgical instrument 100, in accordance with certain embodiments of the present disclosure. The surgical instrument includes a handle 102 that is sized and contoured to be grasped by a hand of a surgeon performing an ophthalmic surgical procedure, including the peeling of a membrane from a retina of a patient's eye, such as an internal limiting membrane (ILM) or epiretinal membrane (ERM). A grasping structure 104 is extendable from a distal end of an outer tube 106 connected to the handle 102, while a proximal end of the outer tube 106 is connected to the handle 102. The handle 102 may have one or more manual control structures mounted thereto. In the embodiment of FIG. 1, the manual control structures include a deformable basket 110. The manual control structure shown is exemplary only, and other manual control structures may also be used (see, for example, FIG. 3).

In FIG. 1, the grasping structure 104 is embodied as forceps comprising a first flexible polymer arm 112 and a second flexible polymer arm 114. The first flexible polymer arm 112 and second flexible polymer arm 114 are connected to an inner rod 116 that is slidably positioned within the outer tube 106. The inner rod 116 may be implemented as a solid rod, or alternatively, as a hollow tube.

In the illustrated embodiments, the first flexible polymer arm 112 has an end 112a fastened to the inner rod 116 either directly or by way of an intermediate arm 116a. The second flexible polymer arm 114 has an end 114a fastened to the inner rod 116 either directly or by way of an intermediate arm 116b. The outer tube 106, inner rod 116, and arms 116a, 116b may be made of nitinol, stainless steel, spring steel, rigid polymer, or other material. In some embodiments, the flexible polymer arms may be made of a softer material than the tubes (e.g., silicone). The arms 116a, 116b may be secured to or monolithically formed with the inner rod 116.

In some embodiments, the deformable basket 110 of the handle 102 is coupled to the outer tube 106. In use, the outer tube 106 may be extended over the first flexible polymer arm 112 and second flexible polymer arm 114 of the grasping structure 104, such as while the outer tube 106 is inserted into or withdrawn from a cannula (e.g., referred to as a trocar cannula) inserted in the patient's eye. Upon releasing compression of the deformable basket 110, the outer tube 106 may then be withdrawn or retracted, thereby extending the inner rod 116 and grasping structure 104 relative to the outer tube 106. Upon compression of the deformable basket 110, the outer tube 106 may be extended over the inner rod 116, thereby retracting the inner rod 116 and grasping structure 104 relative to the outer tube 106. In other embodiments, the deformable basket 110 is coupled to the inner rod 116 and the outer tube 106 is fixed relative to the handle 102. Accordingly, extension of the inner rod 116 and grasping structure 104 may be accomplished by compressing the deformable basket 110, whereas releasing of compression of the deformable basket 110 retracts the inner rod 116 and grasping structure 104 into the outer tube 106.

When extended from the outer tube 106, the first flexible polymer arm 112 and second flexible polymer arm 114 are biased outwardly from one another. The outer tube 106 may be extended relative to the inner rod 116 in order to press the first flexible polymer arm 112 and second flexible polymer arm 114 together and grasp a membrane, e.g., an ILM or ERM.

The first flexible polymer arm 112 and second flexible polymer arm 114 may be made of a highly flexible material, such as thermoplastic elastomer, silicone, or other elastic material. The thermoplastic elastomer may be selected to provide sufficient rigidity to grasp the membrane while being sufficiently soft to reduce risk of puncturing the retina. For example, the thermoplastic elastomer may have a hardness of between about 10 and about 90 Shore A, such as between about 20 and about 80 Shore A, such as between about 30 and about 60 Shore A. The softness of the flexible material forming the flexible polymer arms 112, 114 may be selected in combination with a rigidity of the arms 116a, 116b around which the flexible polymer arms 112, 114 are molded—with increasing softness, the arms 116a, 116b may be made correspondingly more rigid to enable gripping of the membrane. The arms 116a, 116b, when used, may likewise be made of a highly flexible material, such as steel, stainless steel, spring steel, nitinol, or a polymer. The high flexibility enables the first flexible polymer arm 112 and second flexible polymer arm 114, and the arms 116a, 116b when used, to elastically deform in order to fit within the outer tube 106 and, when extended from the outer tube 106, expand to a size that is much wider than an outer diameter of the outer tube 106. For example, the first flexible polymer arm 112 and second flexible polymer arm 114, and the arms 116a, 116b, when used, may expand to at least two times, four times, eight times, or sixteen times the outer dimeter of the outer tube 106 in certain embodiments.

The outer tube 106 defines a longitudinal direction 120a parallel to and collinear with an axis of symmetry of the outer tube 106. The axes of symmetry of the inner rod 116 is substantially (e.g., within 0.5 mm (millimeters)) collinear with the longitudinal direction 120a and substantially (e.g., within 5 degrees of) parallel to the longitudinal direction 120a. A transverse direction 120b may also be defined as perpendicular to the longitudinal direction 120a. A vertical direction 120c may be defined as perpendicular to the longitudinal direction 120a and the transverse direction 120b.

Figures 2A, 2B:
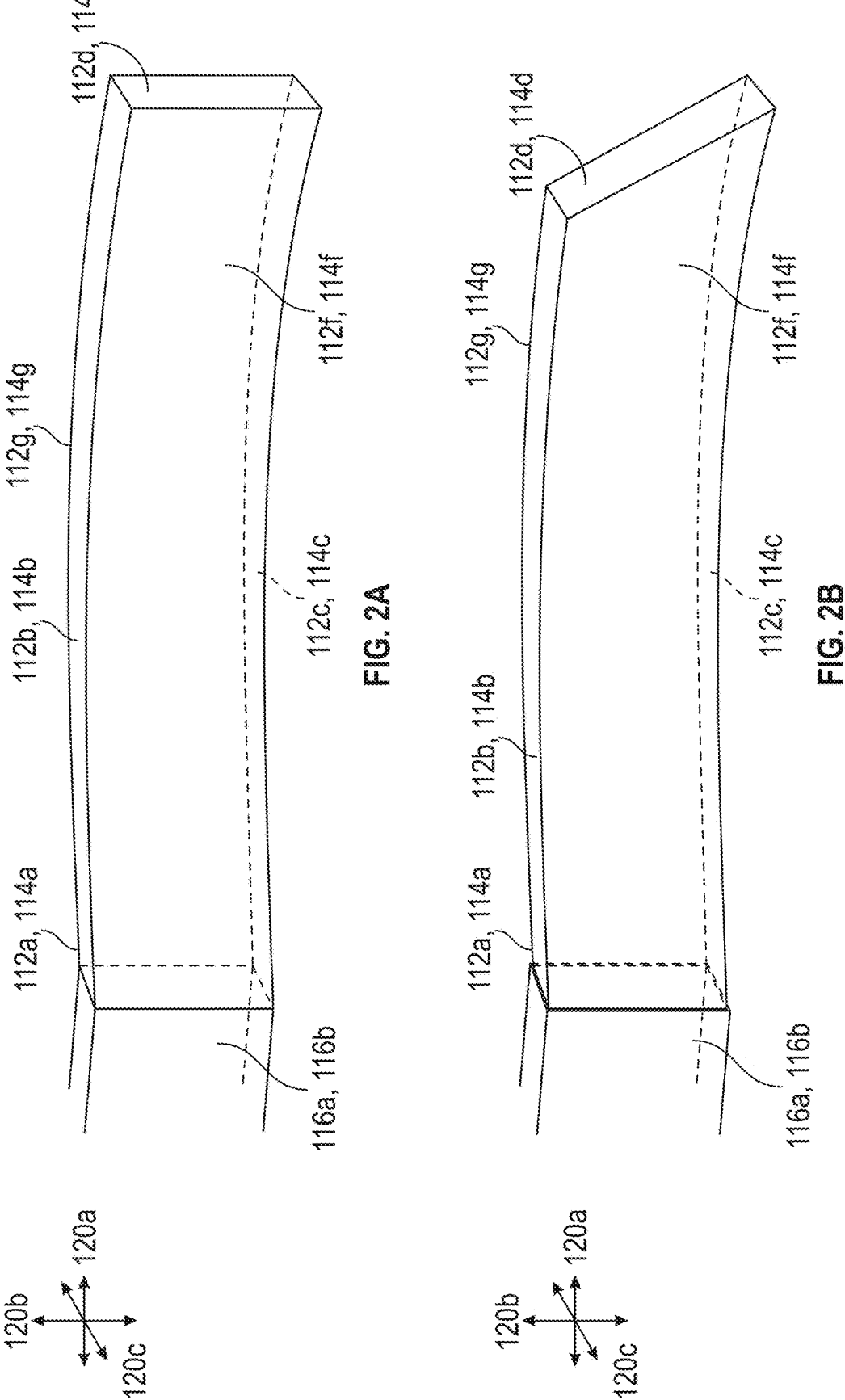
FIG. 2A is an isometric view of an arm of a flexible polymer arm, in accordance with certain embodiments.
FIG. 2B is an isometric view of an alternative shape for a flexible polymer arm, in accordance with certain embodiments.

Referring now to FIGS. 2A and 2B, the flexible polymer arms 112, 114 may have a generally quadrilateral cross section including surfaces 112b, 114b and surfaces 112c, 114c that are substantially (e.g., within 5 degrees) parallel to the longitudinal direction 120a, and the transverse direction 120b ("the longitudinal-transverse plane"). An end surface 112d, 114d extends between the surface 112b, 114b and the surface 112c, 114c of each of the flexible polymer arms 112, 114. In the embodiment of FIG. 2A, the surface 112d, 114d is substantially (e.g., within 5 degrees of) parallel to the vertical direction 120c. In the embodiment of FIG. 2B, the surface 112d, 114d is at an angle with respect to the vertical direction 120c, such as an angle between 10° and 60°, between 20° and 50°, between 30° and 45°, or between 0° and 90°. The flexible polymer arms 112, 114 may also include a grasping platform such as in the 705.43, 705.44, or 705.45 ILM Forceps from ALCON or the MAXGRIP 705.13 forceps from ALCON.

An inner surface 112f, 114f and an outer surface 112g, 114g extend between the surface 112b, 114b and the surface 112c, 114c of each flexible polymer arm 112, 114. In certain embodiments, the inner surface 112f, 114f and/or the outer surface 112g, 114g may be curved in the longitudinal transverse plane and parallel to the vertical direction 120c. The inner surfaces 112f, 114f are generally oriented facing one another and offset from one another in the transverse direction 120b when the grasping structure 104 is extended from the outer tube 106.

The length of the flexible polymer arms 112, 114 between the ends 112a, 114a and the end surfaces 112d, 114d and the flexibility of the material used to form the flexible polymer arms 112, 114 may be selected to enable the flexible polymer arms 112, 114 to deform when placed in contact with the retina or the patient's eye, thereby reducing the risk of puncturing the retina while still providing sufficient rigidity to grasp the membrane. The flexibility of the flexible polymer arms 112, 114 further enables the flexible polymer arms to flex, twist, or otherwise deform to enable the end surfaces 112d, 114d to rest flat on the membrane.

The angle of the end surface 112d, 114d in the embodiment of FIG. 2B may be selected to facilitate placement of the end surface 112d, 114d flat against the retina. In use, the outer tube 106 is inserted through a trocar cannula that is offset from the pupil whereas the membrane is located directly behind the pupil, requiring the outer tube 106 to be angled with respect to the membrane at a point of contact between the grasping structure 104 and the membrane. The angled orientation of the end surface 112d, 114d may therefore compensate for the angle of the outer tube 106 and promote flat placement of the end surface 112d, 114d on the membrane.

The illustrated shapes in FIGS. 2A and 2B are exemplary only. Other shapes, including shapes with rounded rather than quadrilateral shapes, may be used. For example, a round, oval, elliptical, or other cross sectional shape may be used with the distal end surface of such a shape being flat or angled as described above with respect to the end surface 112d, 114d.

Figures 2C, 2D:
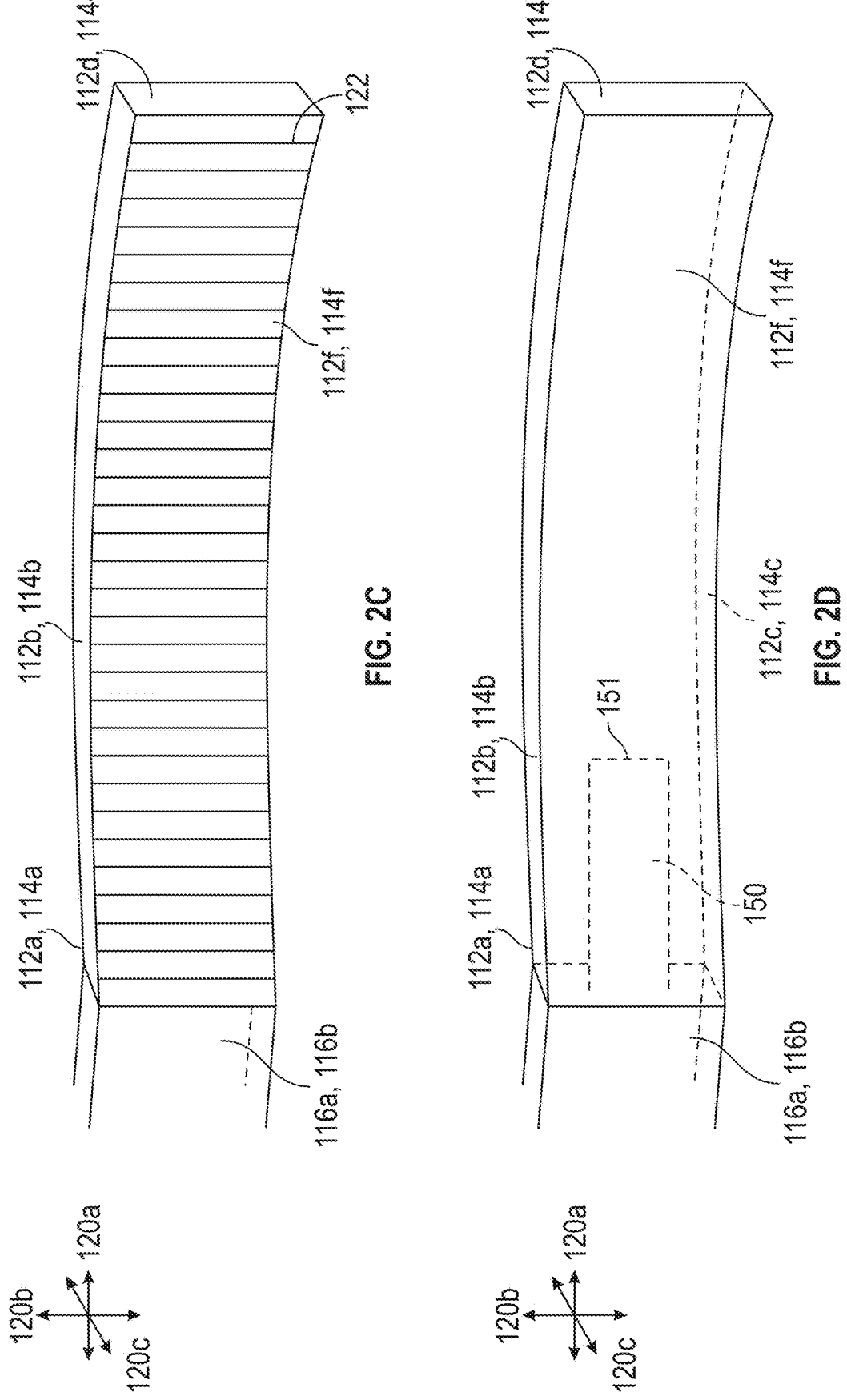
FIG. 2C is an isometric view illustrating texturing on an inner surface of a flexible polymer arm, in accordance with certain embodiments.
FIG. 2D is an isometric view illustrating a flexible polymer arm molded over an extension of an inner tube, in accordance with certain embodiments

Referring now to FIG. 2C, the inner surfaces 112f, 114f of one or both of the first flexible polymer arm 112 and second flexible polymer arm 114 may have texturing formed thereon to facilitate gripping of the membrane. For example, the inner surfaces 112f, 114f may have grooves 122 formed thereon. In the illustrated embodiment, the grooves 122 are oriented parallel to the vertical direction 120c, but grooves having other orientations may additionally or alternatively be used. In this manner, the grooves 122 enhance the ability of the inner surfaces 112f, 114f to grasp a flap raised between the end surfaces 112d, 114d. In other embodiments, texturing may include, but is not limited to, bumps, raised ridges, knurling, or other type of texturing.

Referring to FIG. 2D, the flexible polymer arm 112, 114 may be formed over an extension 150 of the material of the inner rod 116, such as an arm 116a, 116b. In one embodiment, adhesive is added to the outer surface of the extension 150 before the material of the flexible polymer arm 112, 114 is molded over the extension 150. The material of the extension 150 may be the same material as the inner rod 116, including nitinol, stainless steel, spring steel, rigid polymer, or other material. The extension 150 may be a rectangular prism or a cylinder. In certain embodiments, the extension may have texturing to facilitate bonding with the flexible polymer arm 112, 114. The extension 150 extends from the distal end of the inner rod 116, such as an arm 116a, 116b. The material of the flexible polymer arm 112, 114 extends over the extension 150 so that the distal end 151 of the extension 150 is within the material of the flexible polymer arm 112, 114 and does not extend through the flexible polymer arm 112, 114. Stated differently, a portion of the flexible polymer arm 112, 114 extends beyond the extension 150 in the longitudinal direction 120a. The extension 150 have the same flexibility as the flexible polymer arm 112, 114, or may be more or less flexible.

Figure 3:
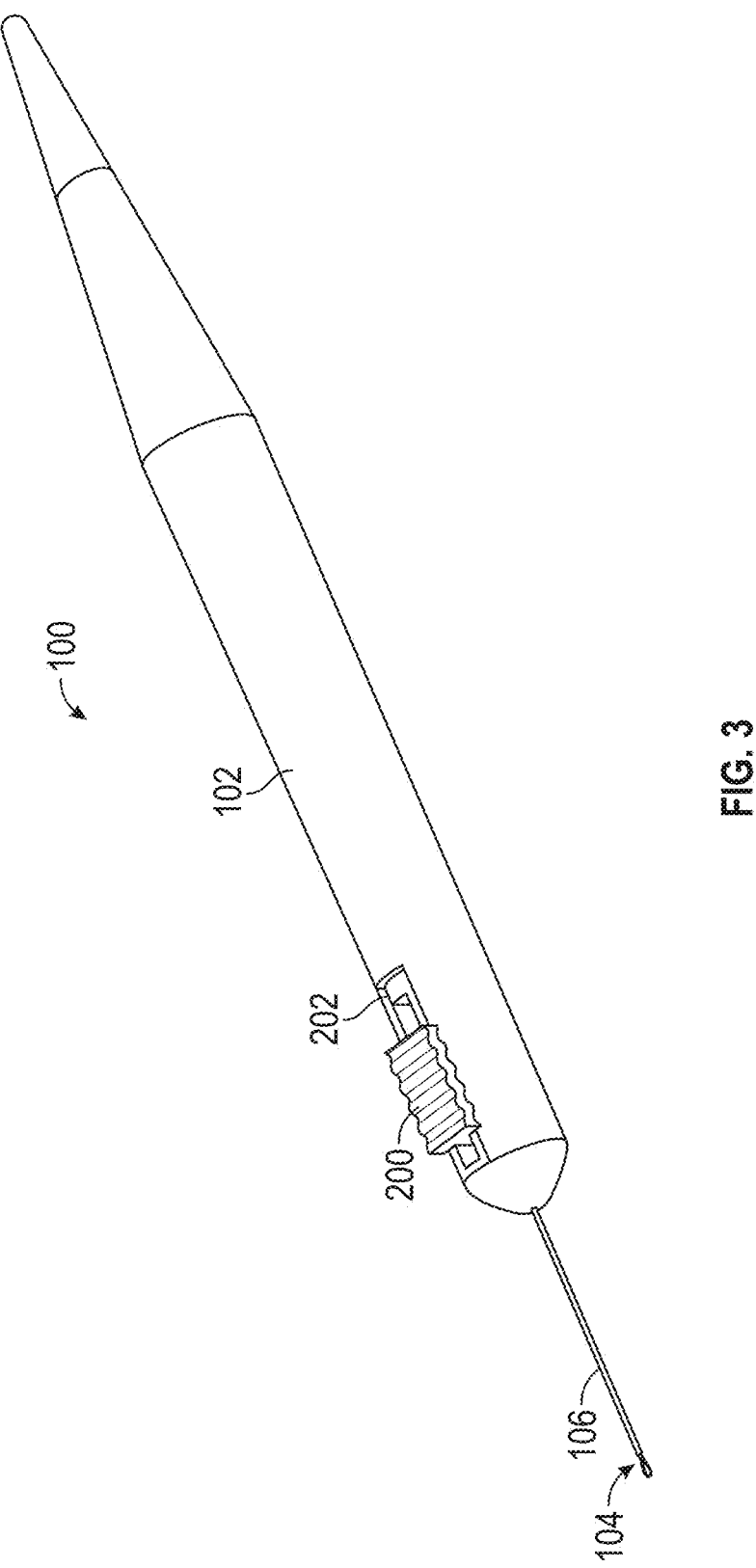
FIG. 3 is an isometric view of an alternative embodiment for actuators for controlling the grasping structure, in accordance with certain embodiments.

Referring to FIG. 3, various actuation mechanisms may be used to control translation of the outer tube 106 and the inner rod 116. In some embodiments, the deformable basket 110 may be replaced with a slider 200 that is slidably mounted to the handle 102. In the illustrated embodiment, the slider 200 slides within a slot 202 defined by the handle 102. In certain embodiments, the slider 200 is coupled to the outer tube 106 and the inner rod 116 is coupled to the handle 102, so that the inner tube is fixed relative to the handle 102, and movement of the slider 200 moves the outer tube 106 over the inner rod 116. In certain embodiments, the slider 200 is coupled to the inner rod 116 and the outer tube 106 is coupled to the handle 102, so that the outer tube 106 is fixed relative to the handle 102, and movement of the slider 200 moves the inner rod 116 within the outer tube 106.

Figure 4A:
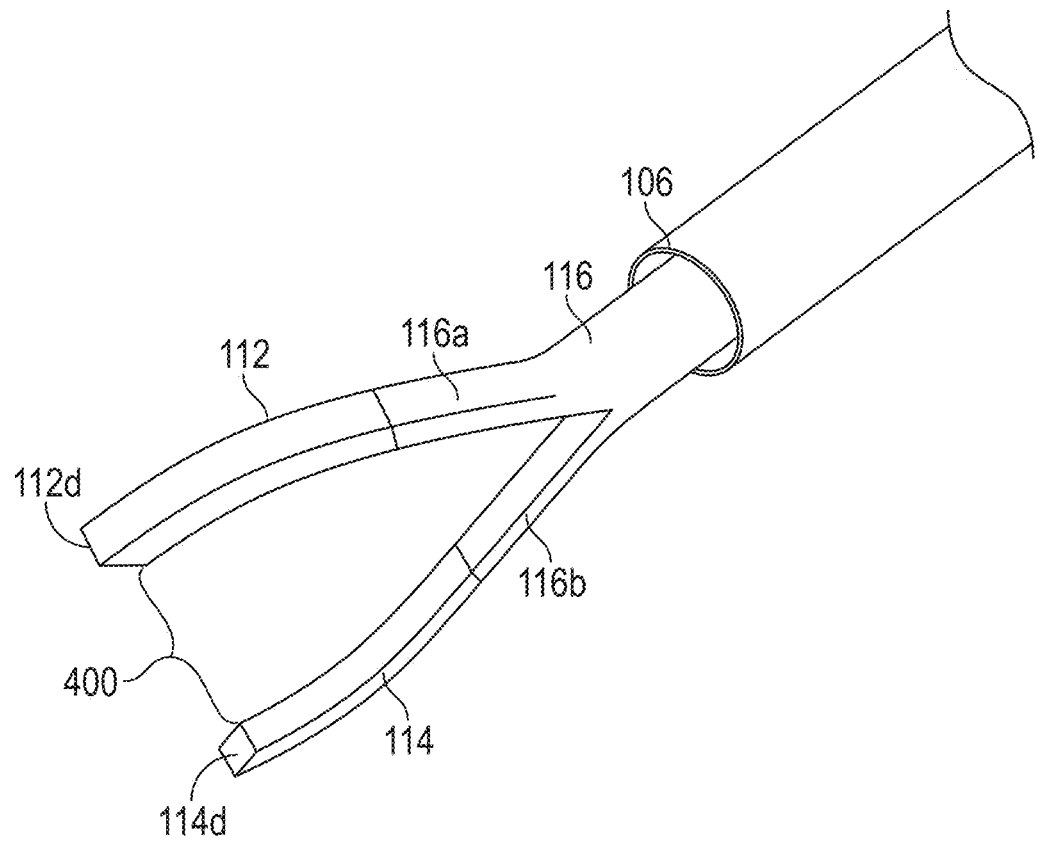
FIG. 4A is an isometric view showing flexible polymer arms in an open configuration, in accordance with certain embodiments.

Referring now to FIG. 4A, in preparation for raising a flap during a procedure, the first flexible polymer arm 112 and the second flexible polymer arm 114 may be positioned in the illustrated "open" configuration with a gap 400 between the end surface 112d and the end surface 114d that is many times greater than the thickness of the membrane (for example, at least 10, 100, or 1000 times the thickness of the membrane).

Figure 4B:
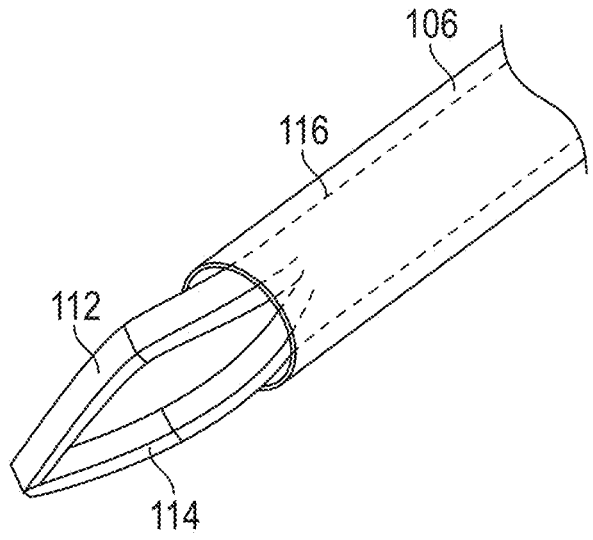
FIG. 4B is an isometric view showing the flexible polymer arms in a closed configuration, in accordance with certain embodiments

Referring to FIG. 4B, the outer tube 106 may be extended partially or completely over the first flexible polymer arm 112 and the second flexible polymer arm 114, or over the arms 116a, 116b, at any point during use of the surgical instrument 100 to form a "closed" position. The stiffness of the first flexible polymer arm 112 and the second flexible polymer arm 114 may be increased by extending the outer tube 106 and reducing the portions of the first flexible polymer arm 112 and the second flexible polymer arm 114 that are positioned outwardly from the outer tube 106. Likewise, where more flexibility is desired, the outer tube 106 may be withdrawn to the point where more, potentially the entirety, of the first flexible polymer arm 112 and the second flexible polymer arm 114 are exposed. In a like manner, the amount of the arms 116a, 116b extending from the outer tube 106 may be controlled in order to control stiffness of the combined flexible polymer arms 112, 114 and arms 116a, 116b.

As noted above, in preparation for insertion of the outer tube 106 through a trocar cannula positioned in an incision in the eye, the outer tube 106 may be extended until either (a) the first flexible polymer arm 112 and the second flexible polymer arm 114 are located completely within the outer tube 106, or (b) the parts the first flexible polymer arm 112 and the second flexible polymer arm 114 extending outwardly form the outer tube 106 are small enough to fit through the cannula (e.g., equal to or smaller than the outer diameter of the outer tube 106).

In the embodiment shown, the forceps (flexible polymer arms 112 and 114 thereof) are slightly curved inward and the end surfaces 112d, 114d are angled such that the end surfaces 112d, 114d meet each other when the forceps are closed. Other embodiments may include different shapes of forceps and/or different angles for end surfaces 112d, 114d. For example, in certain embodiments, the flexible polymer arms 112 and 114 may not curve inward, the flexible polymer arms 112 and 114 may curve outward, or the flexible polymer arms 112 and 114 may be straight or substantially straight.

Figure 5A:
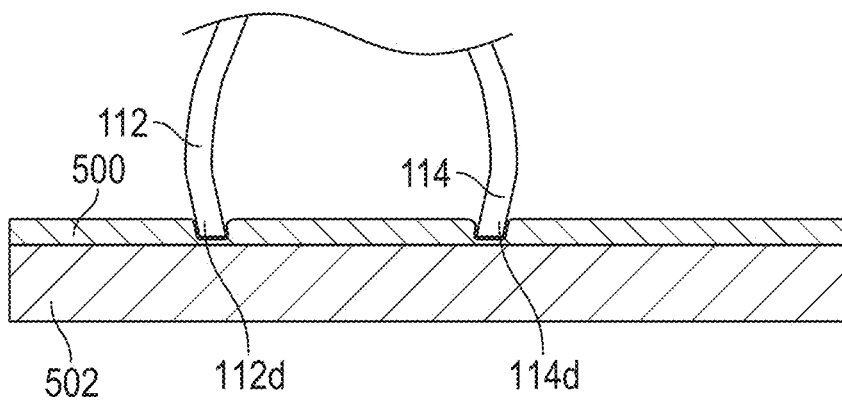
FIGS. 5A to 5C are side cross-sectional views showing the peeling of an ILM using the grasping structure, in accordance with certain embodiments.
Figure 5B:
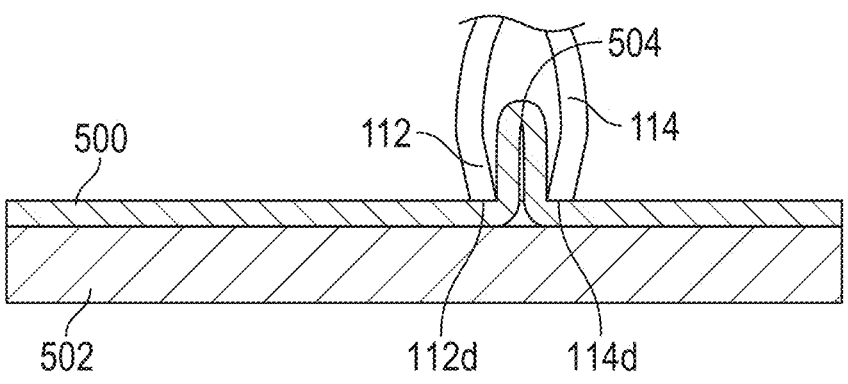
Figure 5C:
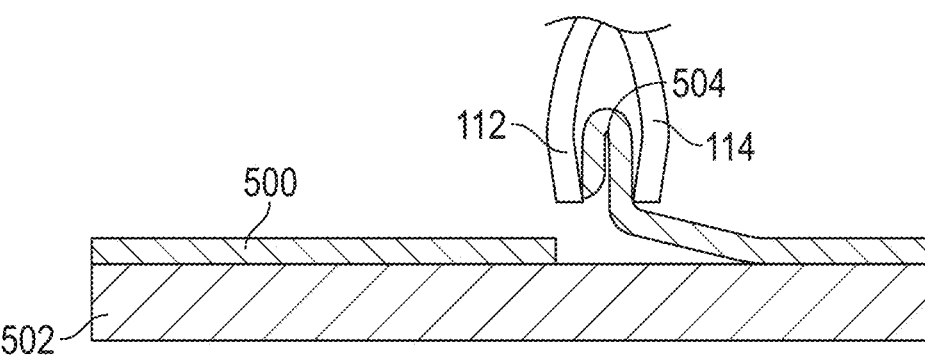
Figure 6:
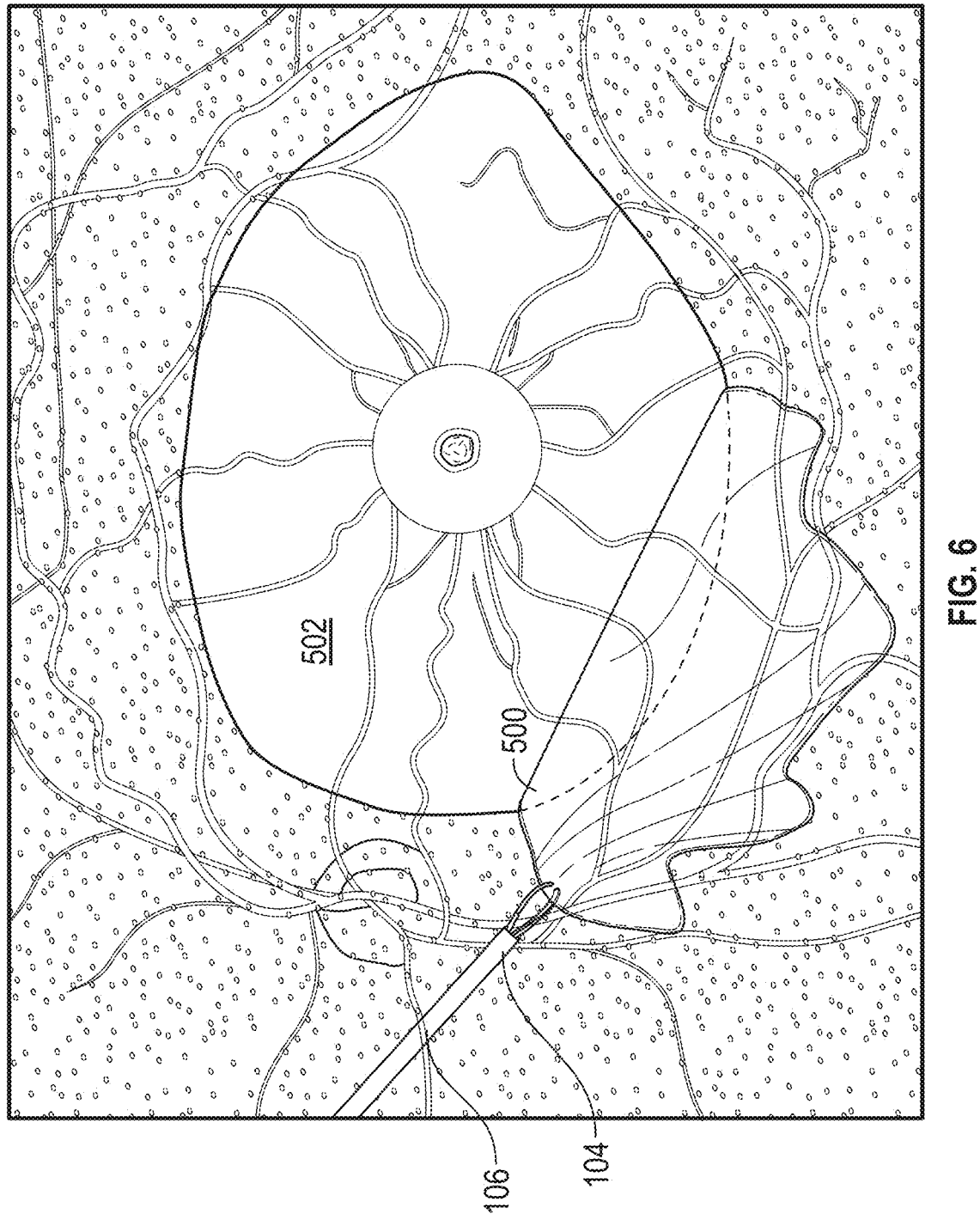
FIG. 6 is an isometric view showing an ILM being peeled using the grasping structure, in accordance with certain embodiments.

Referring to FIG. 5A, during use, lower surfaces of the end surfaces 112d, 114d are pressed downward against the membrane 500 (e.g., ILM or ERM) positioned over the retina 502. Referring to FIG. 5B, a flap 504 may be raised by drawing the end surfaces 112d, 114d towards each other across the membrane 500 in order to grasp the flap 504 firmly. Referring to FIG. 5C, the surgeon may then lift the surgical instrument 100 away from the retina 502 in order to tear the membrane 500. Referring to FIG. 6, the surgeon may move the grasping structure 104 in a circular motion to peel a portion of the membrane 500 away from the retina 502.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. An ophthalmic surgical instrument for peeling a retinal membrane, comprising:
   a handle;
   an actuator mounted on the handle;
   an outer tube having a proximal end mounted to the handle and defining a longitudinal direction;
   an inner rod extending within the outer tube; and
   a grasping structure secured to a distal end of the inner rod, the grasping structure comprising:
   a first polymer arm and a second polymer arm secured to the inner rod and biased outwardly from one another along a transverse direction perpendicular to the longitudinal direction, each of the first polymer arm and the second polymer arm having a generally quadrilateral cross section including pairs of opposing surfaces that are substantially parallel to the longitudinal direction and transverse direction, and a distal end surface extending between the pairs of opposing surfaces that is at an angle between 0 and 90 degrees relative to a vertical direction that is perpendicular to the longitudinal direction and the transverse direction, wherein the actuator is configured to control relative position of the inner rod and the outer tube in order to extend the grasping structure out of the outer tube and withdraw the grasping structure within the outer tube, wherein the inner rod is within a material of the first polymer arm and the second polymer arm without extending through the first polymer arm and the second polymer arm such that portions of the first polymer arm and the second polymer arm extend beyond the inner rod in a longitudinal direction to allow the first polymer arm and the second polymer arm to flex or twist to enable the distal ends of the first polymer arm and the second polymer arm to rest flat on the retinal membrane.

2. The ophthalmic surgical instrument of claim 1, wherein the inner rod is formed of a first material, and the first and second polymer arms are formed of a second material that is different from the first material.

3. The ophthalmic surgical instrument of claim 2, wherein the second material is formed over the first material.

4. The ophthalmic surgical instrument of claim 2, wherein the first material is steel or nitinol.

5. The ophthalmic surgical instrument of claim 2, wherein the second material is a thermoplastic elastomer.

6. The ophthalmic surgical instrument of claim 5, wherein the thermoplastic elastomer has a hardness between Shore A 10 and 90.

7. The ophthalmic surgical instrument of claim 2, further comprising a first arm formed on the inner rod and a second arm formed on the inner rod, the first arm and the second arm comprising the first material, the first polymer arm being secured to the first arm and the second polymer arm being secured to the second arm.

8. The ophthalmic surgical instrument of claim 7, wherein:

the first arm has a first extension formed thereon, the first polymer arm being molded over the first extension; and the second arm has a second extension formed therein, the second polymer arm being molded over the second extension.

9. The ophthalmic surgical instrument of claim 1, wherein the first polymer arm and the second polymer arm are configured to elastically deform sufficiently to fit within the outer tube.

10. The ophthalmic surgical instrument of claim 1, at least one of the first polymer arm and the second polymer arm are textured to improve gripping of a membrane on a retina of a patient's eye.

11. The ophthalmic surgical instrument of claim 1, wherein the inner rod is fixed relative to the handle and the outer tube is fixed relative to the actuator.

12. The ophthalmic surgical instrument of claim 1, wherein the first polymer arm and the second polymer arm are configured to expand to a size more than two times an outer diameter of the outer tube when extended from the outer tube.

13. The ophthalmic surgical instrument of claim 1, wherein the first polymer arm and the second polymer arm are configured to expand to a size more than four times an outer diameter of the outer tube when extended from the outer tube.

14. A method for peeling a membrane from a retina of a patient's eye, the method comprising:

inserting a distal end of an outer tube through a cannula in the patient's eye;

extending a grasping structure from the outer tube along a longitudinal direction, the grasping structure secured to an inner rod and having a first polymer arm and a second polymer arm secured to the inner rod and biased outwardly from one another along a transverse direction perpendicular to the longitudinal direction, each of the first polymer arm and the second polymer arm having a generally quadrilateral cross-section including pairs of opposing surfaces that are substantially parallel to the longitudinal direction and transverse direction, and a distal end surface extending between the pairs of opposing surfaces that is at an angle between 0 and 90 degrees relative to a vertical direction that is perpendicular to the longitudinal direction and the transverse direction;

pressing the distal end of the first polymer arm and the distal end of the second polymer arm against the membrane; and withdrawing the grasping structure at least partially into the outer tube thereby urging the first polymer arm and the second polymer arm together in order to form a flap of the membrane and grasp the flap between the first polymer arm and the second polymer arm;

wherein the inner rod is within a material of the first polymer arm and the second polymer arm without extending through the first polymer arm and the second polymer arm such that portions of the first polymer arm and the second polymer arm extend beyond the inner rod in a longitudinal direction to allow the first polymer arm and the second polymer arm to flex or twist to enable the distal ends of the first polymer arm and the second polymer arm to rest flat on the retinal membrane.

15. The method of claim 14, further comprising pulling on the flap effective to peel a portion of the membrane from the retina.

16. The method of claim 14, wherein the outer tube is mounted to a handle having an actuator mounted thereto and coupled to the outer tube, the method comprising moving the actuator to extend the grasping structure from the outer tube and retract the grasping structure within the outer tube.

17. The method of claim 14, wherein the inner rod comprises nitinol and the first and second polymer arms comprise a thermoplastic elastomer.

* * * * *